United States Patent [19]

Partenheimer

[11] Patent Number: 4,719,311
[45] Date of Patent: Jan. 12, 1988

[54] PROCESS FOR THE PRODUCTION OF AROMATIC POLYCARBOXYLIC ACIDS

[75] Inventor: Walter Partenheimer, Naperville, Ill.

[73] Assignee: Amoco Corporation, Chicago, Ill.

[21] Appl. No.: 790,538

[22] Filed: Oct. 23, 1985

[51] Int. Cl.$^4$ .............................................. C07C 51/21
[52] U.S. Cl. ..................................... 562/413; 562/416
[58] Field of Search .................................. 562/416, 413

[56] References Cited

U.S. PATENT DOCUMENTS

| 4,197,412 | 4/1980 | Kimura et al. | 562/416 |
| 4,230,882 | 10/1980 | Seko et al. | 562/416 |
| 4,299,977 | 11/1981 | Kuhlmann et al. | 562/416 |

Primary Examiner—Werren B. Lone
Attorney, Agent, or Firm—Gunar J. Blumberg; William H. Magidson; Ralph C. Medhurst

[57] ABSTRACT

A process for the manufacture of polycarboxylic acids having at least three carboxylic acid groups for each benzene ring is disclosed. In this novel process, water is used in the last third of the reaction to improve the yield of cobalt-manganese-bromine or oxidation system and eliminate catalyst deactivation. Polycarboxylic acids such as durene are converted to pyromellitic acid which is used to manufacture a polyimide ring used as molding compounds for replacement of metals.

12 Claims, 1 Drawing Figure

FIG. I
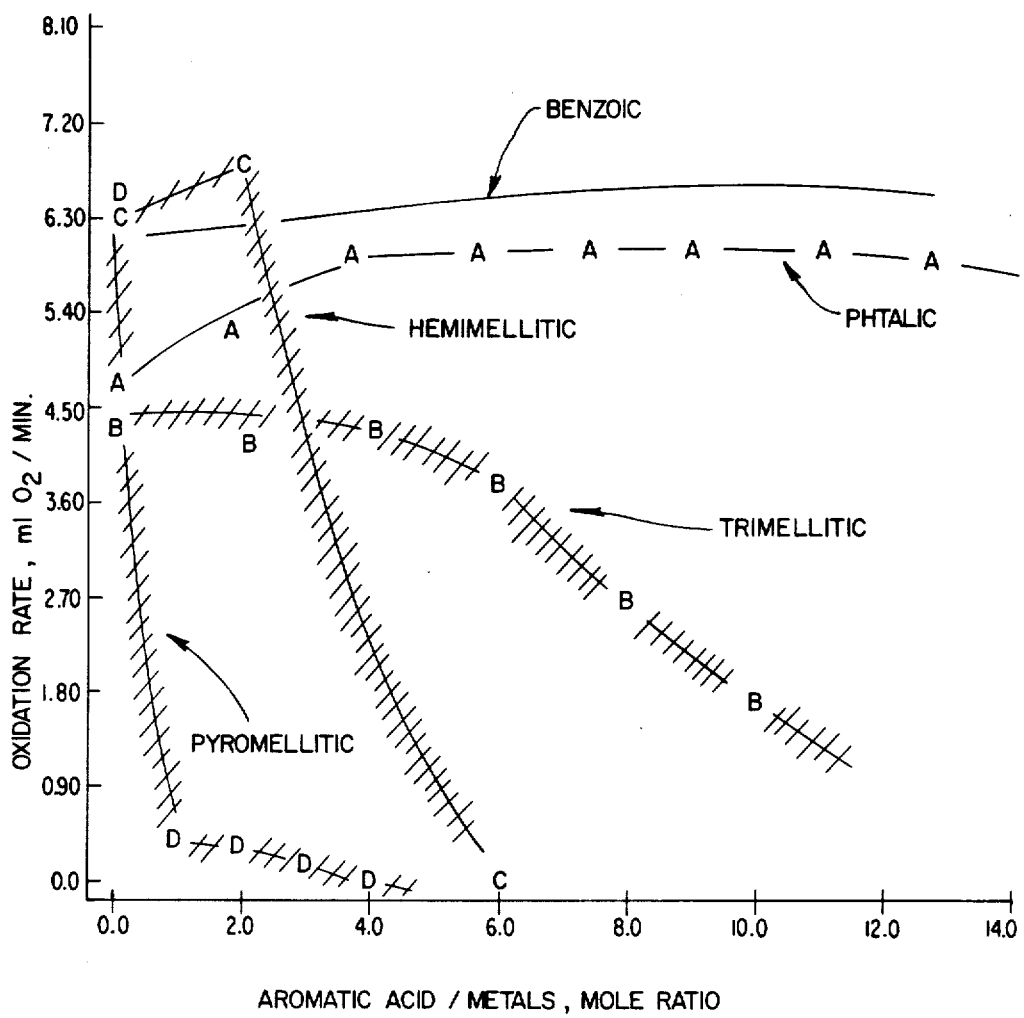
ADDITION OF SELECTED AROMATIC ACIDS TO A
Co/Mn/Br CATALYZED OXIDATION OF PSEUDOCUMENE
AT A WATER LEVEL OF 0.3 %

PROCESS FOR THE PRODUCTION OF AROMATIC POLYCARBOXYLIC ACIDS

BACKGROUND

The field of this invention relates to the liquid-phase oxidation of polyalkyl aromatics to their corresponding polycarboxylic acids. More particularly, the invention relates to the oxidation of tri, tetra, penta, and hexamethylbenzenes to their corresponding polycarboxylic acids in high yields.

We have not been able to achieve high yields of the polycarboxylic acid when polymethylbenzenes having three or more methyl substituents are oxidized to their corresponding polycarboxylic acids in the presence of a cobalt, manganese, and bromine catalyst utilizing a hydrocarbon solvent. This is particularly critical when polymethylbenzenes have four or more methyl substituents.

The reasons for this are not clear but the polycarboxylic acids produced when tri, tetra, penta, and hexamethylene are oxidized have a propensity to precipitate the cobalt and manganese from the reaction mixture. The cobalt, manganese, and bromine catalyst is also deactivated when the polycarboxylic acids have two carboxylic groups ortho to each other on the benzene ring. For durene, the deactivation of the catalyst occurs when the oxidation of durene to pyromellitic acid is about fifty percent complete. In polycarboxylic acids having more carboxylic acid groups ortho to each other, the catalyst deactivation occurs at conditions when the oxidation reaction is less than fifty percent complete. I have overcome these disadvantages by adding about 0.3 to 0.7 grams of water per gram of reaction mass, the preferred amount being about 0.4 to 0.6 grams of water per gram of reaction mass. The addition of the water takes place during the last third of the reaction, preferably just prior to completion of the reaction.

A process for oxidizing polyalkylaromatics having between 3 and 6 methyl groups on each benzene ring to their corresponding acids which comprises catalytically oxidizing the polyalkylaromatic feedstock with air in the presence of an aliphatic acid in an oxidation zone wherein liquid-phase conditions are maintained and wherein the weight ratio of aliphatic acid to the polyalkylaromatic is in the range of about 0.5–4:1.0 and the catalyst comprises one or more heavy metal oxidation catalysts and a source of bromine, the process comprises addition of a combination of sources of cobalt, manganese, and bromine components to provide about 0.05 to about 2.0 weight percent total metals on the polyalkylaromatic feedstock wherein there is present a weight ratio of bromine ions to total metal ions of about 0.5–8.0:1.0, a manganese content of about 10–50 percent by weight of the total metals, and the reaction is conducted at a temperature of about 100° C. to about 275° C. and about 0.3 to about 0.7 grams of water are added during the last third of the reaction per gram of total reactants. A process for oxidizing durene to pyromellitic acid which comprises catalytically oxidizing pyromellitic feedstock with air in the presence of an aliphatic acid in an oxidation zone wherein liquid-phase conditions are maintained and wherein the weight ratio of aliphatic acid to durene is in the range of about 0.5–4:1.0 and the catalyst comprises one or more heavy metal oxidation catalysts and a source of bromine, the process comprises addition of a combination of sources of cobalt, manganese, and bromine components to provide about 0.2 to about 0.4 weight percent total metals based on durene wherein there is present a weight ratio of bromine ions to total metal ions of about 0.5–3.0:1.0, a manganese content of about 10–50 percent by weight of the total metals, and the reaction is conducted at a temperature of about 100° C. to about 275° C. and about 0.3 to about 0.7 grams of water are added during the last third of the reaction per gram of the total reactants.

In the batchwise oxidation of the aromatic compounds having about 3 to 6 methyl units on each benzene ring the exothermic heat of reaction vaporizes some of the liquid solvent which is carried out of the reactor by the process air. The solvent is condensed and returned to the reactor as reflux. This liquid reflux is reheated toward the end of the reaction cycle to ensure temperatures high enough to bring the oxidation to completion. After reaction, the reactor contents are depressurized and the polycarboxylic acid is crystallized out to form a 50–60% solids slurry (close to the maximum solids concentration that is pumpable). The solids are filtered out and further processed into final product. My process is particularly suitable for the oxidation of alkyl aromatics having three or more methyl groups on each benzene ring to their corresponding polycarboxylic acids. The following hydrocarbons are particularly suitable as feedstock for my novel process: 1,2,4-trimethylbenzene, 1,2,3-trimethylbenzene, 1,2,3,4-tetramethylbenzene, 1,2,3,5-tetramethylbenzene, 1,2,3,4,5-pentamethylbenzene, and 1,2,3,4,5,6-hexamethylbenzene.

The oxidation of the alkyl aromatics such as durene, tetramethylbenzene, pentamethylbenzene, and hexamethylbenzene is conducted batchwise. All of the hydrocarbon feedstock and most (90–99%) of the acetic acid and initial amount of catalyst components are charged at or near oxidation initiation temperature, preferably at about 100° C. to about 165° C., and at a pressure to maintain liquid-phase conditions. Then, pressurized air is injected into the reaction mixture and the reaction temperature is permitted to increase by heat evolved by the oxidation reaction to about 175° C. to about 250° C.

The total bromine added can be from a single source of bromine, for example, ionic bromine sources (HBr, NaBr, NH$_4$Br, and the like) or from a combined form of bromine, for example, organic bromines such as benzyl bromine, tetrabromoethane, and others.

My novel process relates to the liquid-phase oxidation of alkyl aromatics to polycarboxylic acids, particularly the oxidation of durene to pyromellitic acid using cobalt, manganese, plus bromine. A useful catalyst for my process is a cobalt-manganese-bromine catalyst and the oxidation is conducted at a temperature in the range of about 100° C. to about 250° C., which process comprises conducting a batch oxidation of durene so that the concentration of bromine in the first stage is 0 to about 0.5 mole per mole of metals while all the remaining bromine is added during the second stage. The total amount of bromine added is about 50 to about 800 weight percent of the total metal catalysts present, the reaction is completed in a non-continuous process at a temperature of about 140° C. to about 250° C.

The water about 0.4 to 0.6 grams per gram of reaction mass is added during the last third of the reaction. The preferred embodiment of my process comprises conducting a batch oxidation of the hydrocarbon so that in the first stage no bromine is added or the amount of bromine added is below 30 weight percent of the total bromine to be added. The reaction is completed in a non-continuous process at a temperature of about 120° C. to about 250° C. and during the last 5 to about 20 percent of the reaction time.

My novel process also relates to the liquid-phase oxidation of aromatic hydrocarbons having three or more alkyl groups attached to the benzene ring using cobalt, manganese, plus bromine. My novel invention is a process for the oxidation of tri, tetra, penta, and hexamethylbenzenes with molecular oxygen to benzene tetra, penta, of hexacarboxylic acid under liquid-phase conditions in the presence of a cobalt-manganese-bromine catalyst at a temperature in the range of about 100° C. to about 250° C.

The commercial process for the production of terephthalic acid, isophthalic acid, and trimellitic acid from p-xylene, m-xylene, and pseudocumene (1,2,4-trimethylbenzene), respectively, uses dioxygen as the oxidant, a soluble mixture of cobalt, manganese, and bromide as a catalyst, and acetic acid as the solvent. I have found that when other selected feedstocks are oxidized to aromatic acids, using this same process, that the aromatic acids severely inhibit and even prevent the reaction from occurring. This is because the aromatic acid precipitates the catalyst metals, cobalt, and manganese. For example, when durene is oxidized to pyromellitic acid, the pyromellitic acid concentration begins to increase near the end of the reaction and this acid precipitates the metals and prematurely stops the reaction before all of the durene is reacted. This results in low yields to pyromellitic acid. I have discovered a novel, unobvious method for preventing the precipitation of the metals. This novel procedure is the rapid addition of water near the end of the reaction. Water is a product of the oxidation of polyalkylbenzenes to aromatic acids, and the art of homogeneous oxidation teaches that its concentration should be minimized. It should be minimized because water is a catalyst deactivator. In this invention, we minimize the water concentration in the reactor until catalyst precipitation begins to occur. Then, I perform a process which is contrary to the teachings of the art—to add water rapidly to the reactor. I will now illustrate that: (1) catalyst metals are precipitated by certain aromatic acids in acetic acid, (2) that they become more soluble as the water concentration in the acetic acid increases, (3) that one can visually observe catalyst precipitation during a homogeneous oxidation, and that concomitant with catalyst precipitation, the reaction rate severely decreases, and (4) the rapid addition of water at the end of an oxidation of durene results in high yields of pyromellitic acid.

Table I illustrates that pyromellitic acid (1,2,4,5-tetracarboxybenzene, the product of durene oxidation) precipitates cobalt(II) acetate and manganese (II) acetate from a typical solution used in homogeneous oxidation. A typical water concentration inside a reactor during a homogeneous oxidation is about 20%. Example 21 on Table I illustrates that at this water concentration, using sodium bromide as the bromide source, 62% of the cobalt has precipitated and 93% of the manganese has precipitated. Similar results are illustrated for hemimellitic acid (the product of 1,2,3-trimethylbenzene) on Table II and for trimellitic acid (the product of pseudocumene) on Table III. Importantly, Tables I–III also illustrate that the catalyst precipitation ceases after a certain amount of water has been added to the acetic acid. For pyromellitic acid and hemimellitic acid this limit is about 40% water in the acetic acid, while for trimellitic acid the limit is about 20% (using hydrogen bromide as the bromide source--sodium bromide has higher limits).

FIG. 1 illustrates that the precipitation of the catalyst metals retards the rate of oxidation and, if in high enough concentrations, completely inhibits the reaction. The homogeneous oxidation is purposely made to occur very slowly so that the rate of oxidation would be constant for a number of hours. While the homogeneous oxidation is in progress, increments of selected acids are added. Acids such as benzoic and phthalic have little effect on the rate of oxidation and no precipitation occurs in the glass reactor. However, addition of trimellitic, hemimellitic, and pyromellitic causes precipitation of the metals in the reactor and, at first, severely inhibits the reaction, and when in sufficient concentration, causes the oxidation to cease.

The following examples illustrate the preferred embodiment of this invention. It will be understood that the examples are for illustrative purposes only and do not purport to be wholly definitive with respect to the conditions and scope of the invention.

EXAMPLE 1

The experiments for the oxidation of the durene was performed in a two liter autoclave equipped with a stirrer, air line, cooling coil, and an additional line for addition of reagents during the oxidation. The temperature of the reactor is controlled by insulated electrical heaters which surround the autoclave, and the cooling coil in the reactor. A controlled rate of fluid is passed through the cooling coil during the oxidation. The vented gases from the reactor are passed through a series of condensers, cooled by dry-ice, and then through instruments which record the gaseous flow rate and the concentration of dioxygen and carbon dioxide in the gas stream. In a typical experiment, the reagents are added to the autoclave and the reactor purged with a slow addition of nitrogen gas. The reactor is brought up to the initiation temperature and then the reaction started by stopping the nitrogen gas flow and starting a flow of air through the reactor. The pressure of the reactor is controlled by a research control valve. Reagents were added into the autoclave during the reaction by a suitable pump. The reaction is terminated by the addition of a flow of nitrogen gas into the reactor.

Table IV gives a typical time-temperature-pressure profile during a batch oxidation of durene. A pump is used to slowly add a catalyst mixture dissolved in a solvent. At 50 minutes, when the durene is approximately 80% oxidized and significant amounts of pyromellitic acids are starting to form in the reactor, the rate of the pump is greatly increased so that the water concentration is rapidly increased inside the reactor. Catalyst metals are placed in the pump solution so that the deactivating effect of the water can be compensated by additional catalyst. Examples 55–58 illustrate the effect of increasing the pump rate into the reactor after 50 minutes into the reaction. This increases the water content at the end of the oxidation (see Table V) and results in the yield increasing from 66 to 80 molar % pyromellitic acid. The level of reaction intermediates, the sum of the dicarboxyphthalide and tricarboxyltoluene, drop from 19.6 to 14.4 to 9.94 to 1.6, indicating that the reaction has gone increasingly farther to completion. This can also be seen by the increase in acid number of the solids obtained after the reactor effluent is cooled. In examples 55–58 the increase is 834, 845, 860 to 878 (883 is the theoretical value for 100% pure pyromellitic acid). The beneficial effect of water can also be seen by comparing example 58 and 64. In example 64 the water in the pump has been replaced by acetic acid. This resulted in a large decrease in the amount of water added to the reactor and the yield decreased from 80 to 64% with a concomitant decrease in the acid number from 878 to 853. Examples 57 and 63 are similar. The other examples on Table VI use varying amounts of catalyst in the pump solution and also give high yields to pyromellitic acid and high acid numbers.

Procedure for FIG. 1

Homogeneous oxidations were performed in a glass reactor in which air was passed through the acetic acid via a glass frit. 100.0 ml of acetic acid, 10.0 ml of pseudocumene, 0.002 mol of cobalt(II) acetate tetrahydrate, 0.002 mol of manganese(II) acetate tetrahydrate, 0.004 mol of sodium bromide were initially placed in the reactor. The water and the selected aromatic acid were added incrementally during the oxidation. The temperature of the reaction was 95° C., the pressure ambient atmospheric, and the flow rate of air 52 ml/min. The rate of oxidation was determined by measuring the oxygen content of the vent gas and knowing the flow rate of air through the reactor.

TABLE I

The Solubility of Cobalt(II), Manganese(II), and Bromide in Acetic acid-Water Mixtures in the Presence of Pyromellitic acid (1,2,4,5-tetracarboxybenzene)(3)

| Example | Reaction Number | Water in HOAc, % | % of Dissolved Metal(4) | | | Bromine Source | Ppt., gms |
|---|---|---|---|---|---|---|---|
| | | | Co | Mn | Br | | |
| 1 | 10290-84-1 | 0 | 45 | 23 | 81 | HBr | 10.84(1) |
| 2 | 9355-178-1 | 20 | 98 | 96 | 93 | HBr | none,(2),(4) |
| 3 | 10290-84-2 | 20 | 81 | 57 | 89 | HBr | 0.875 |
| 4 | 9358-190-1 | 20 | 81 | 56 | 95 | HBr | 0.64 |
| 5 | 9355-178-2 | 20 | 87 | 30 | 89 | HBr | 0.87 |
| 6 | 10290-84-3 | 25 | 65 | 76 | 96 | HBr | 0.68 |
| 7 | 9358-190-2 | 25 | 59 | 88 | 90 | HBr | 0.63 |
| 8 | 10290-84-4 | 30 | 83 | 91 | 95 | HBr | 0.41 |
| 9 | 9358-190-3 | 30 | 66 | 87 | 95 | HBr | 0.61 |
| 10 | 9358-190-4 | 35 | 96 | 95 | 97 | HBr | 0.11 |
| 11 | 9358-190-5 | 40 | 100 | 96 | 98 | HBr | 0.05 |
| 12 | 9355-178-4 | 40 | 141 | 102 | 87 | HBr | 0.16 |
| 13 | 9355-178-6 | 40 | 102 | 95 | 94 | HBr | 0.12 |
| 14 | 9358-190-6 | 50 | 102 | 96 | 97 | HBr | 0.06 |
| 15 | 9355-178-5 | 60 | 99 | 92 | 92 | HBr | 0.12 |
| 16 | 9358-190-7 | 60 | 93 | 92 | 97 | HBr | 0.08 |
| 17 | 9358-190-8 | 70 | 94 | 94 | 97 | HBr | 0.04 |
| 18 | 9358-190-9 | 80 | 94 | 91 | 97 | HBr | 0.03 |
| 19 | 9358-190-10 | 90 | 104 | 96 | 94 | HBr | 0.04 |
| 20 | 9358-190-11 | 100 | 93 | 89 | 89 | HBr | 0.02 |
| 21 | 9355-178-3 | 20 | 38 | 7.2 | 81 | NaBr | 1.33 |
| 22 | 9358-190-14 | 20 | 32 | 32 | 87 | NaBr | 1.20 |
| 23 | 9358-190-15 | 30 | 45 | 66 | 92 | NaBr | 0.92 |
| 24 | 9358-190-16 | 40 | 49 | 82 | 94 | NaBr | 0.72 |
| 25 | 9358-190-17 | 60 | 100 | 97 | 91 | NaBr | 0.09 |
| 26 | 9358-190-18 | 100 | 100 | 93 | 91 | NaBr | 0.03 |

(1)not all of the pyromellitic was soluble in the acetic acid.
(2)no pyromellitic acid was added to catalyst metals and bromide.
(3)Procedure: 0.047 mol of pyromellitic acid was dissolved in 100.0 ml of the acetic acid/water mixture at 95° C. 0.024 mol of cobalt(II) acetate tetrahydrate, 0.024 mol of manganese(II) acetate tetrahydrate, 0.048 mol of the bromide source, and 0.000185 mol of zirconium(IV) oxide acetate was then added to the dissolved pyromellitic acid with continuous stirring. After 15 minutes the mixture was filtered into a hot funnel. The solids were air dried and weighed. 50 ml of water was added to the filtrate and the filtrate analyzed for the elements of interest.
(4)This was determined by dividing the moles of metal present in solution after the experiment by the moles added initially, expressed on a percentage basis.

TABLE II

The Solubility of Cobalt(II), Manganese(II), and Bromide in Acetic acid-Water Mixtures in the Presence of Hemimellitic acid (1,2,3-tricarboxybenzene)(1)

| Example | Reaction Number | Water in HOAc, % | % of Dissolved Metal | | | Bromine Source | Ppt., gms |
|---|---|---|---|---|---|---|---|
| | | | Co | Mn | Br | | |
| 27 | 10290-92-1 | 0 | 51 | 11 | 90 | HBr | 1.09 |
| 28 | 10290-92-2 | 5 | 64 | 34 | 94 | HBr | 0.79 |
| 29 | 10290-92-3 | 10 | 52 | 59 | 92 | HBr | 1.11 |
| 30 | 10290-92-4 | 15 | 35 | 66 | 92 | HBr | 1.44 |
| 31 | 10290-92-5 | 20 | 50 | 70 | 91 | HBr | 1.07 |
| 32 | 10290-92-6 | 30 | 79 | 89 | 92 | HBr | 0.847 |
| 33 | 10290-92-7 | 40 | 108 | 107 | 96 | HBr | 0.14 |
| 34 | 10290-92-8 | 50 | 101 | 98 | 96 | HBr | 0.012 |
| 35 | 10290-92-9 | 0 | 68 | 15 | 92 | NaBr | 0.866 |
| 36 | 10290-92-10 | 5 | 71 | 31 | 93 | NaBr | 0.696 |
| 37 | 10290-92-11 | 10 | 51 | 51 | 92 | NaBr | 1.11 |
| 38 | 10290-92-12 | 15 | 33 | 61 | 96 | NaBr | 1.49 |
| 39 | 10290-92-13 | 20 | 54 | 66 | 91 | NaBr | 1.13 |
| 40 | 10290-92-14 | 30 | 60 | 74 | 91 | NaBr | 1.04 |

(1)The procedure and amounts of chemicals are identical to that on Table 1 except that the pyromellitic is replaced by hemimellitic acid.

TABLE III

The Solubility of Cobalt(II), Manganese(II), and Bromide in Acetic acid-Water Mixtures in the Presence of Trimellitic acid.

| Example | Reaction Number | Water in HOAc, % | % of Dissolved Metal | | | Bromine Source | Ppt., gms |
|---|---|---|---|---|---|---|---|
| | | | Co | Mn | Br | | |
| 41 | 10290-86-A | 0 | 61 | 50 | 92 | HBr | 5.63(1) |
| 42 | 10290-86-B | 5 | 63 | 53 | 94 | HBr | 2.48(1) |
| 43 | 10290-86-C | 10 | 89 | 89 | 97 | HBr | 0.183 |
| 44 | 10290-86-D | 15 | 87 | 92 | 99 | HBr | 0.030 |
| 45 | 10290-86-E | 20 | 99 | 99 | 98 | HBr | 0.024 |
| 46 | 10290-86-F | 30 | 99 | 94 | 96 | HBr | 0.036 |
| 47 | 10290-86-G | 40 | 98 | 94 | 93 | HBr | 0.042 |
| 48 | 10290-86-H | 50 | 96 | 96 | 91 | HBr | 0.050 |
| 49 | 10290-86-I | 0 | 20 | 5.1 | 84 | NaBr | 5.90(1) |
| 50 | 10290-86-J | 5 | 24 | 13 | 81 | NaBr | 2.62(1) |
| 51 | 10290-86-K | 10 | 76 | 30 | 93 | NaBr | 0.981 |
| 52 | 10290-86-L | 15 | 90 | 54 | 92 | NaBr | 0.595 |
| 53 | 10290-86-M | 20 | 99 | 98 | 89 | NaBr | 0.079 |
| 54 | 10290-86-N | 30 | 99 | 94 | 92 | NaBr | 0.074 |

(1)Not all of the trimellitic acid was soluble prior to catalyst metals addition.

The procedure and amounts of chemicals are identical to that on Table 1 except that the pyromellitic acid is replaced by trimellitic acid.

TABLE IV

Typical Reaction of Durene in an Autoclave With Continuous Addition of Catalyst and Solvent(1)

| Time, Min. | Flow Rate of Air, Cubic ft/min | Pressure lbs/in² | Temp., °F. | Solution Pumped Into the Reactor | | |
|---|---|---|---|---|---|---|
| | | | | Water, g | Manganese, mmol | Bromide, mmol |
| 0 | 0.78 | 150 | 280 | 0 | 0 | 0 |
| 5 | 0.78 | 150 | 282 | 3 | 0.064 | 1.0 |
| 10 | 0.78 | 150 | 292 | 6 | 0.14 | 2.0 |
| 15 | 0.78 | 150 | 300 | 9 | 0.21 | 3.0 |
| 20 | 0.78 | 200 | 305 | 12 | 0.28 | 4.1 |
| 25 | 0.78 | 200 | 312 | 15 | 0.35 | 5.1 |
| 30 | 0.78 | 225 | 317 | 18 | 0.42 | 6.1 |
| 35 | 0.78 | 250 | 325 | 21 | 0.49 | 7.1 |
| 40 | 0.78 | 275 | 327 | 24 | 0.56 | 8.1 |
| 45 | 0.78 | 300 | 350 | 27 | 0.62 | 9.1 |
| 50 | 0.78 | 350 | 400 | 30 | 0.69 | 10.1 |
| 55 | 0.48 | 400 | 428 | 70 | 1.62 | 23.8 |
| 60 | 0.48 | 450 | 438 | 110 | 2.54 | 37.3 |
| 65 | 0.48 | 450 | 442 | 150 | 3.47 | 50.9 |

TABLE IV-continued

Typical Reaction of Durene in an Autoclave With Continuous Addition of Catalyst and Solvent(1)

| Time, Min. | Flow Rate of Air, Cubic ft/min | Pressure lbs/in$^2$ | Temp., °F. | Solution Pumped Into the Reactor | | |
|---|---|---|---|---|---|---|
| | | | | Water, g | Manganese, mmol | Bromide, mmol |
| 70 | 0.48 | 450 | 439 | 190 | 4.39 | 64.4 |
| 75 | 0.48 | 450 | 439 | 230 | 5.32 | 78.1 |
| 80 | 0.48 | 450 | 440 | 270 | 6.24 | 91.6 |
| 85 | 0.48 | 450 | 440 | 310 | 7.17 | 105 |
| 90 | 0.48 | 450 | 440 | 360 | 8.32 | 122 |
| 95 | 0.48 | 450 | 437 | 400 | 9.25 | 136 |
| 100 | 0.48 | 450 | 436 | 400 | 9.25 | 136 |
| 105 | 0.48 | 450 | 435 | 400 | 9.25 | 136 |
| 110 | 0.48 | 450 | 435 | 400 | 9.25 | 136 |

(1)Results of Table IV are given in example 58 in tables V and VI

TABLE V

Amounts of Reagents Used in The Autoclave Reactions

| Example | 55 | 56 | 57 | 58 | 59 |
|---|---|---|---|---|---|
| Notebook Page No. | 8363 162 | 8363 166 | 8363 186 | 8363 190 | 8363 194 |
| Initial Charge in Reactor | | | | | |
| Durene, g | 184.24 | 184.24 | 184.24 | 184.24 | 184.24 |
| Acetic acid, g | 400 | 400 | 400 | 400 | 400 |
| Water, g | 21 | 21 | 21 | 21 | 21 |
| Cobalt, mmol | 13.1 | 13.1 | 13.1 | 13.1 | 13.1 |
| Manganese, mmol | 4.1 | 4.1 | 4.1 | 4.1 | 4.1 |
| HBr, mmol | 3.1 | 3.1 | 3.1 | 3.1 | 3.1 |
| Zirconium, mmol | 0.198 | 0.198 | 0.198 | 0.198 | 0.198 |
| Added During Reaction Via Pump | | | | | |
| Acetic acid, g | 68.8 | 0 | 0 | 0 | 0 |
| Water, g | 12.5 | 97.1 | 166.1 | 365 | 381 |
| Cobalt, mmol | 0 | 0 | 0 | 0 | 30.9 |
| Manganese, mmol | 2 | 2.5 | 4.2 | 9.3 | 9.6 |
| HBr, mmol | 28.5 | 35.2 | 60.5 | 132.9 | 138.2 |
| Zirconium, mmol | 0.596 | 0.745 | 1.286 | 2.833 | 2.795 |

| Example | 60 | 61 | 62 | 63 | 64 |
|---|---|---|---|---|---|
| Notebook Page No. | 8363 197 | 9685 1 | 9685 4 | 9685 10 | 9685 19 |
| Initial Charge in Reactor | | | | | |
| Durene, g | 184.24 | 184.24 | 184.24 | 184.24 | 184.24 |
| Acetic acid, g | 400 | 400 | 400 | 399 | 400 |
| Water, g | 21 | 21 | 21 | 21 | 21 |
| Cobalt, mmol | 13.1 | 13.1 | 13.1 | 13.1 | 13.1 |
| Manganese, mmol | 4.1 | 4.1 | 4.1 | 4.1 | 4.1 |
| HBr, mmol | 3.1 | 3.1 | 3.3 | 3.1 | 3.1 |
| Zirconium, mmol | 0.198 | 0.198 | 0.198 | 0 | 0.198 |
| Added During Reaction Via Pump | | | | | |
| Acetic acid, g | 0 | 0 | 0 | 180 | 240 |
| Water, g | 369 | 341 | 443 | 0 | 0 |
| Cobalt, mmol | 59.8 | 0 | 0 | 0 | 0 |
| Manganese, mmol | 18.7 | 8.6 | 11.2 | 4.3 | 5.8 |
| HBr, mmol | 267.6 | 123.4 | 160.8 | 62.4 | 83.1 |
| Zirconium, mmol | 5.74 | 1.325 | 3.448 | 1.334 | 1.782 |

TABLE VI

Results from the Batch Oxidations of Durene

| Example | 55 | 56 | 57 | 58 | 59 |
|---|---|---|---|---|---|
| Notebook Page No. | 8363 162 | 8363 166 | 8363 186 | 8363 190 | 8363 194 |
| Molar Yield, % | | | | | |
| Pyromellitic Acid | 66 | 66 | 71 | 80 | 80 |
| Trimellitic Acid | 1.66 | 0.74 | 1.48 | 1.41 | 1.46 |
| 1,2-dicarboxy-phthalide | 8.48 | 6.16 | 4.03 | 1.12 | 1.29 |
| 2,4,5-tricarboxy toluene | 11.14 | 8.28 | 5.91 | 0.52 | 0.58 |
| Acid No. (1) | 834 | 845 | 860 | 878 | 871 |
| % Burning of hydrocarbon (2) | 4 | 4.6 | 4.9 | 7.4 | 7.1 |

| Example | 60 | 61(3) | 62(3) | 63 | 64 |
|---|---|---|---|---|---|
| Notebook Page No. | 8363 197 | 9685 1 | 9685 4 | 9685 10 | 9685 19 |
| Molar Yield, % | | | | | |
| Pyromellitic Acid | 83 | 82 | 83 | 71 | 64 |
| Trimellitic Acid | 1.64 | 1.09 | 2.07 | 1.99 | 2.51 |
| 1,2-dicarboxy-phthalide | 1.03 | 1.05 | 1.08 | 5.64 | 3.6 |
| 2,4,5-tricarboxy toluene | 0.32 | 0.29 | 0.4 | 12.69 | 8.34 |
| Acid No. (1) | 870 | 870 | 874 | 845 | 853 |
| % Burning of hydrocarbon | 7.4 | 6.8 | 6.8 | 3.9 | 5.6 |

(1) The theoretical acid number of pyromellitic acid is 883. The acid number is on the solids that precipitate from the mother liquor. These solids were dried for 2 hrs. at 100° C. before the acid number measurement.
(2) 75% of the observed carbon dioxide content of the vent is assumed to be from the complete combustion of the durene.
(3) A gaseous feed composition using 30% oxygen was used instead of air which contains 20.9% oxygen. This resulted in a faster rate of oxidation so that the total run time was 75 min. rather than the usual 110 min.

I claim:

1. A process for oxidizing polyalkylaromatic hydrocarbons having between 3 and 6 methyl groups on each benzene ring to their corresponding acids which comprises catalytically oxidizing the polyalkylaromatic hydrocarbon feedstock with air in the presence of an aliphatic acid in an oxidation zone wherein liquid-phase conditions are maintained and wherein the weight ratio of aliphatic acid to the polyalkylaromatic hydrocarbon is in the range of about 0.5–4.0:1.0 and the catalyst comprises cobalt, manganese and bromine, the process comprises addition of a combination of cobalt, manganese, and bromine components to provide about 0.05 to about 2.0 weight percent total metals based on the polyalkylaromatic hydrocarbon feedstock wherein there is present a weight ratio of bromine ions to total metal ions of about 0.5–8.0:1.0, a manganese content of about 10–50 percent by weight of the total metals, and the reaction is conducted at a temperature of about 100° C. to about 275° C. and about 0.3 to about 0.7 grams of water are added during the last third of the reaction per gram of total reactants.

2. The method of claim 1 wherein the aliphatic acid is acetic acid.

3. The process of claim 1 or claim 2 wherein the oxidation is conducted in two stages and most of the bromine is added in the second stage.

4. A process for oxidizing durene to pyromellitic acid which comprises catalytically oxidizing durene with air in the presence of an aliphatic acid in an oxidation zone wherein liquid-phase conditions are maintained and wherein the weight ratio of aliphatic acid to durene is in the range of about 0.5–4.0:1.0 and the catalyst comprises cobalt, manganese and bromine, the process comprises addition of a combination of cobalt, manganese, and bromine components to provide about 0.2 to about 0.4 weight percent total metals based on durene wherein there is present a weight ratio of bromine ions to total metal ions of about 0.5–3.0:1.0, a manganese content of about 10–50 percent by weight of the total metals, and the reaction is conducted at a temperature of about 100° C. to about 275° C. and about 0.3 to about 0.7 grams of water are added during the last third of the reaction per gram of total reactants.

5. The method of claim 4 wherein the aliphatic acid is acetic acid.

6. The process of claim 4 or claim 5 wherein the oxidation is conducted in two stages and most of the bromine is added in the second stage.

7. The process of claim 1 wherein the hydrocarbon feedstock is tetramethylbenzene.

8. The process of claim 1 wherein the hydrocarbon feedstock is pentamethylbenzene.

9. The process of claim 1 wherein the hydrocarbon feedstock is hexamethylbenzene.

10. The process of claim 1 wherein the hydrocarbon feedstock is trimethylbenzene.

11. The process of claim 1 wherein the reaction is conducted at a temperature of about 100° C. to about 250° C.

12. The process of claim 4 wherein the reaction is conducted at a temperature of about 100° C. to about 250° C.

* * * * *

UNITED STATES PATENT OFFICE
CERTIFICATE OF CORRECTION

Patent No. 4,719,311               Dated January 12, 1988

Inventor(s) WALTER PARTENHEIMER

It is certified that error appears in the above-identified patent and that said Letters Patent are hereby corrected as shown below:

| Col. | Line | |
|---|---|---|
| 4 | 27 | "was performed" should be -- were performed-- |
| 5 | 67 | "filtate and the filtate" should be --filtrate and the filtrate-- |
| 6 | 22 | "pyromellitic is" should be --pyromellitic acid is-- |

Signed and Sealed this

Twenty-eighth Day of June, 1988

*Attest:*

DONALD J. QUIGG

*Attesting Officer*     *Commissioner of Patents and Trademarks*